United States Patent [19]
Minklei

[11] 3,965,201

[45] June 22, 1976

[54] FLUORINATION OF HEXACHLOROBUTADIENE

[75] Inventor: Alfred O. Minklei, Grand Island, N.Y.

[73] Assignee: Hooker Chemicals & Plastics Corporation, Niagara Falls, N.Y.

[22] Filed: Oct. 11, 1973

[21] Appl. No.: 405,723

[52] U.S. Cl. .............................. 260/653.4; 252/442
[51] Int. Cl.² ................. C07C 17/04; C07C 17/20; C07C 21/04
[58] Field of Search ................................. 260/653.4

[56] References Cited
UNITED STATES PATENTS

| | | |
|---|---|---|
| 3,149,170 | 9/1964 | Clark et al. ...................... 260/653.4 |
| 3,258,500 | 6/1966 | Swamer et al. .................. 260/653.4 |
| 3,395,187 | 7/1968 | Christoph, Jr. .................. 260/653.4 |
| 3,413,360 | 11/1968 | Gardner ........................... 260/653.4 |
| 3,541,165 | 11/1970 | Vecchio et al. .................. 260/653.4 |

*Primary Examiner*—D. Horwitz
*Attorney, Agent, or Firm*—Peter F. Casella; William J. Crossetta, Jr.; Eric C. Cohen

[57] ABSTRACT

Hexachlorobutadiene is fluorinated with hydrogen fluoride in the presence of a fluorinated alumina catalyst to yield 2,3-dichlorohexafluorobutene-2 (butene-26).

2 Claims, No Drawings

FLUORINATION OF HEXACHLOROBUTADIENE

The present invention relates to a process of producing 2,3-dichlorohexafluorobutene-2 (butene-26). Butene-26 may be oxidized to trifluoroacetic acid by known methods. Butene-26 may be converted to perfluorobutene and perfluorobutane by the following reactions:

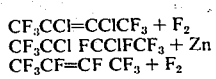   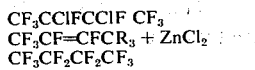

$CF_3CCl=CClCF_3 + F_2$    $CF_3CClFCClF\ CF_3$
$CF_3CCl\ FCClFCF_3 + Zn$    $CF_3CF=CFCF_3 + ZnCl_2$
$CF_3CF=CF\ CF_3 + F_2$    $CF_3CF_2CF_2CF_3$

The present process is superior to present methods known and practiced in the art for producing butene-26 in that the present process produces a high yield of butene-26 without a substantial amount of by-products, such as 2 chloroheptafluorobutene-2, which require rather citical separation techniques. The present invention utilizes an inexpensive catalyst, fluorinated alumina, as compared to the generally used catalysts containing chromium. Thus the catalyst recovery aspect is not as economically critical and the product may be utilized without a purification step to remove chromium.

The present process comprises contacting a vapor phase mixture of hexachlorobutadiene, chlorine and hydrogen fluoride with a fluorinated alumina catalyst at a temperature of between about 300° and about 550°C and recovering 2,3-dichlorohexafluorobutene-2.

The process may be conducted either continuously or batchwise. In a preferred embodiment the reaction components are passed in vapor form through a bed of the fluorinated catalyst which is suitably contained in a stainless steel or nickel-pipe reactor. The product gases are processed through a water scrubber, a drying unit and subsequently into a refrigerated trap where the product mixture is condensed and recovered. The components of the product mixture may suitably be separated by distillation.

The process temperature can vary between about 300° and about 550°C with a preferred temperature range between about 400° and about 500°C. The process may be carried out at pressures higher or lower than atmospheric pressure. Higher pressures are more desirable in that productivity is increased and such conditions facilitate the recovery of hydrogen chloride by-product and other lower boiling materials. Pressures up to 200 p.s.i.g. and higher may advantageously be employed.

The particle size of the catalyst is preferably between 6 and 30 mesh. A material of between 8 and 20 mesh is emiently suited to the present process. The surface area of the catalyst, the thickness of the catalyst bed and the velocity of the gas flow through the bed are dependent variables. Thus a catalyst particle size of between 6 and 30 mesh is aptly suited to a bed thickness of between about 2 inch and about 6 inch with a gas flow, expressed in terms of space velocity of between about 300 and 7000 liters per liter of catalyst per hour.

The residence time of the feed mixture in the reaction zone may also vary widely depending upon the reaction temperature and composition of the feed mixture. The residence time may range from as low as 1.0 second at higher reaction temperatures to several minutes at lower reaction temperature. In operations utilizing a reaction temperature between about 400° and about 500°C a residence time of between about 7 and about 10 seconds is suitable.

The molar ratio of hydrogen fluoride and chlorine to hexachlorobutadiene may vary broadly in the range of between about 8 to 12 moles of hydrogen fluoride to about 1 to 3 moles of chlorine to about 1 to 2 moles of hexachlorobutadiene.

The life of the catalyst employed in the present invention does not appear to be affected by operating temperatures as high as 450° to 550°C. The catalyst life of prior art catalysts falters and is substantially shortened in this range.

The alumina catalyst of the present invention may be prepared by dissolving $Al_2O_3$ in a strong base such as sodium hydroxide or potassium hydroxide. This solution is then reacted with a strong acid, such as hydrochloric acid, to produce a gel. Suitably this is done by simultaneously adding the alumina solution and the strong acid to a holding vessel containing water. Preferably the pH is maintained between about 7 and 9 during this addition. The proportions of the reaction components are adjusted so that at the final pH the gel remains in the range of from about 7 to about 9. The gel is then recovered by filtration and dried. The dried alumina material is treated with hydrogen fluoride. Suitably such treatment is carried out by flowing hydrogen fluoride through the dried alumina material. An exposure time of from 8 to 20 hours at a temperature of between 350° and 500°C produces a catalyst useful in the process of the present invention.

The product of the present process may be recovered from the effluent gases by scrubbing with water, drying in the presence of a drying agent such as calcium chloride and condensing in a dry ice trap. The condensed product may then be washed and dried and the components separated by distillation. The expected yield of butene-26 from the present process is between about 80 to 90% based upon the weight of the hexachlorobutadiene starting material.

The following examples serve to illustrate the invention, but are not intended to limit the invention.

EXAMPLE 1

This example illustrates the preparation of the alumina catalysts useful in carrying out the process of the present invention.

250 grams of $Al_2O_3.3H_2O$ was dissolved in a 30.93% by weight solution of sodium hydroxide at the boiling point. This solution was then added, simultaneously, with a 23.7% by weight solution of hydrochloric acid to 2500 ml of water. The pH was maintained between 7 and 9 during the addition step and the final pH was adjusted to about 8.7. A slurry was formed. The slurry was then recovered by filtration and washed until there was an absence of a saline taste. The washed slurry cake was then dried overnight at 72°C.

A dried slurry cake as prepared above was then ground. 330 ml of 8-20 mesh material was obtained by screening. This material was placed in a 1 inch ID nickel reactor and calcined overnight at 400°C under a nitrogen purge. Hydrogen fluoride was than passed through the material for 14.3 hours at a temperature of 375°C.

EXAMPLE 2

A gaseous mixture of 0.53 mole of hexachlorobutadiene, 5.4 moles of hydrogen fluoride and 0.79 mole of chlorine was passed through the reactor and catalyst as prepared in Example 1 for 4 hours at a reactor temperature of 450°C. The mixture had a residence time of 8.8 seconds. The effluent gas was collected in a water trap, dried, condensed in a dry ice trap and the condensate distilled. A total of 109 grams of material was collected. The reaction product was found to be 86% by weight 2,3-dichlorohexafluorobutene-2, 0.5% unreacted hexachlorobutadiene, 8.4% of materials boiling below butene-26 and below hexachlorobutadiene.

What is claimed is:

1. A process which comprises the steps or reacting in the vapor phase a mixture comprised of hexachlorobutadiene, hydrogen fluoride and chlorine at a temperature between about 300°C and about 550°C in the presence of a particulate fluorinated alumina catalyst and recovering 2,3-dichlorohexafluorobutene-2 as product, said catalyst being prepared by the steps of dissolving alumina in a strong base, treating the resulting solution with a strong acid, to form a gel, recovering and drying the gel to produce a dried product and, treating the dried product with hydrogen fluoride at a temperature of between 350° and 500°C to fluorinate the dried product.

2. The process of claim 1 wherein the yield of 2,3-dichlorohexafluorobutene-2 is at least 85% by weight.

* * * * *